United States Patent [19]

Shiokawa et al.

[11] Patent Number: 4,920,129
[45] Date of Patent: Apr. 24, 1990

[54] ANTI-ULCERATIVE IMIDAZOPYRIDINE COMPOUNDS

[75] Inventors: Youichi Shiokawa, Ibaraki; Masanobu Nagano, Kawanishi; Hiromichi Itani, Osaka, all of Japan

[73] Assignee: Fujisawa Pharmaceutical Company, Ltd., Osaka, Japan

[21] Appl. No.: 247,657

[22] Filed: Sep. 22, 1988

[30] Foreign Application Priority Data

Sep. 24, 1987 [GB] United Kingdom ................ 8722488

[51] Int. Cl.$^5$ ..................... A61K 31/44; C07D 471/04
[52] U.S. Cl. ..................................... 514/300; 546/121
[58] Field of Search ......................... 546/121; 514/300

[56] References Cited

U.S. PATENT DOCUMENTS 4,725,601 2/1988 Ueda et al. ........................... 546/121
4,831,041 5/1989 Shiokawa et al. ................... 546/121

Primary Examiner—Richard A. Schwartz
Assistant Examiner—Bernard I. Dentz
Attorney, Agent, or Firm—Oblon, Spivak, McClelland, Maier & Neustadt

[57] ABSTRACT

The invention relates to an imidazopyridine compound of the following formula:

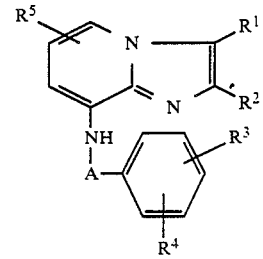

wherein $R^1$ is lower alkynyl, $R^2$ is lower alkyl, $R^3$ is lower alkyl, $R^4$ is amino or acylamino, $R^5$ is hydrogen; lower alkyl which may be substituted by halogen, halogen; nitro; amino; acylamino; esterified carboxy; or N,N-di(lower)alkylsufamoyl, and A is lower alkylene, and pharmaceutically acceptable salts thereof, useful in the treatment of ulcers.

14 Claims, No Drawings

ANTI-ULCERATIVE IMIDAZOPYRIDINE COMPOUNDS

The present invention relates to novel imidazopyridine compound and a pharmaceutically acceptable salt thereof. More particularly, it relates to novel imidazopyridine compound and a pharmaceutically acceptable salt thereof which have antiulcerative activity, to a process for preparation thereof, to pharmaceutical composition comprising the same, and to method of using the same therapeutically in the treatment of ulcer in human being or animals.

Accordingly, one object of the present invention is to provide novel imidazopyridine compound and a pharmaceutically acceptable salt thereof, which are useful as a medicine for ulcer.

Another object of the present invention is to provide a process for preparation of said imidazopyridine compound or a pharmaceutically acceptable salt thereof.

A further object of the present invention is to provide pharmaceutical composition comprising, as an active ingredient, said imidazopyridine compound or a pharmaceutically acceptable salt thereof.

Still further object of the present invention is to provide method of using said imidazopyridine compound or a pharmaceutically acceptable salt thereof in the treatment of ulcer in human being or animals.

The imidazopyridine compound of the present invention is novel and can be represented by the formula (I):

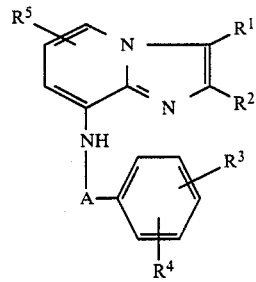

wherein
$R^1$ is lower alkynyl,
$R^2$ is lower alkyl,
$R^3$ is lower alkyl,
$R^4$ is amino or a protected amino,
$R^5$ is hydrogen, lower alkyl which may have suitable substituent(s), halogen, nitro, amino, a protected amino, a protected carboxy or N,N-di(lower)alkylsulfamoyl, and
A is lower alkylene.

According to the present invention, the object compound (I) can be prepared by the following processes.

Process 1

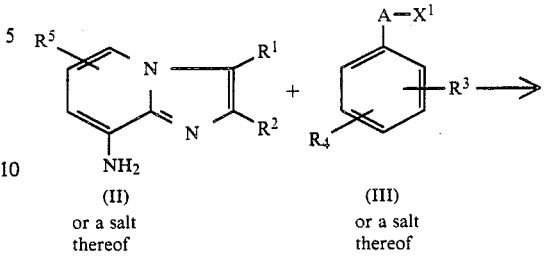

Process 2

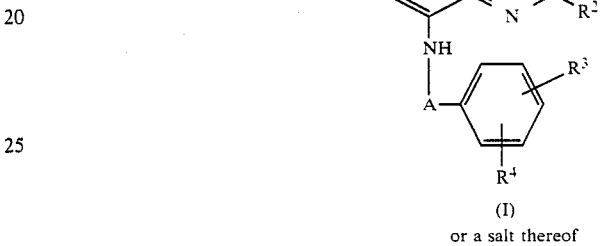

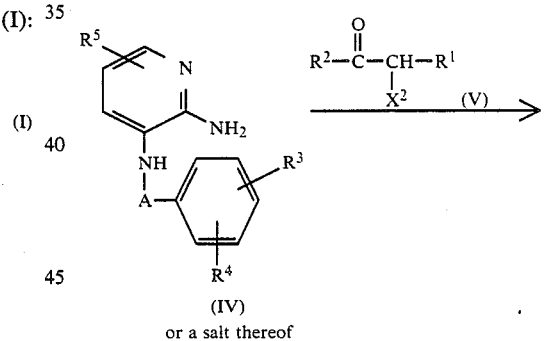

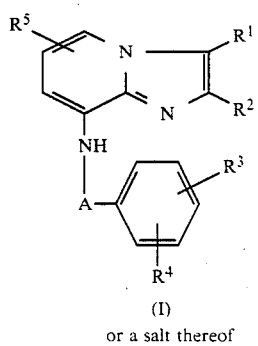

Process 3

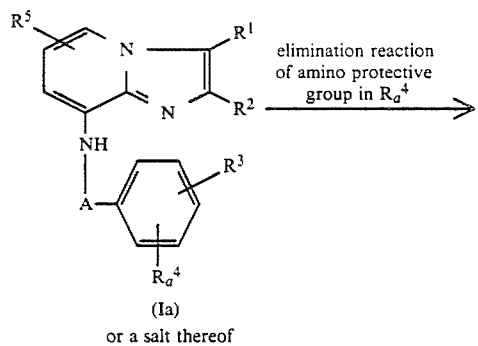
(Ia)
or a salt thereof
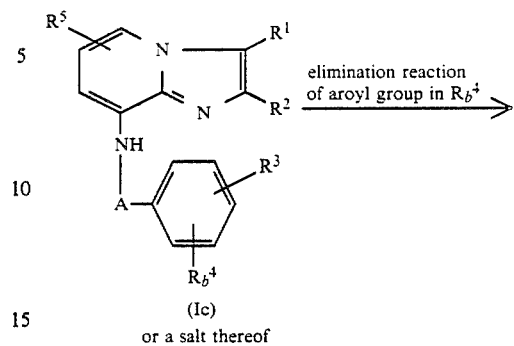
(Ic)
or a salt thereof
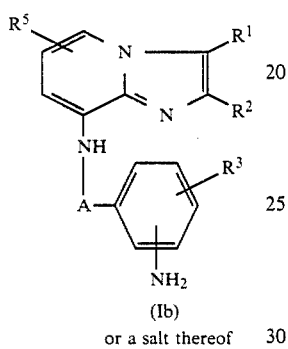
(Ib)
or a salt thereof
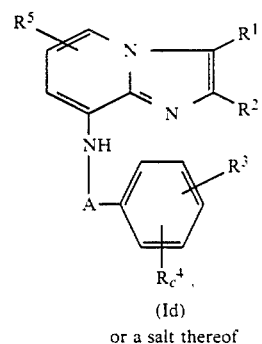
(Id)
or a salt thereof
Process 4
Process 6
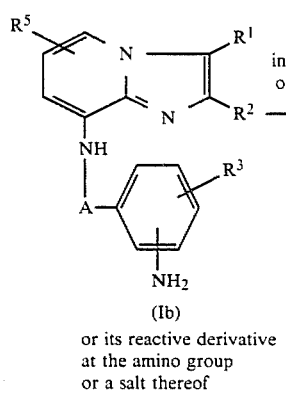
(Ib)
or its reactive derivative
at the amino group
or a salt thereof
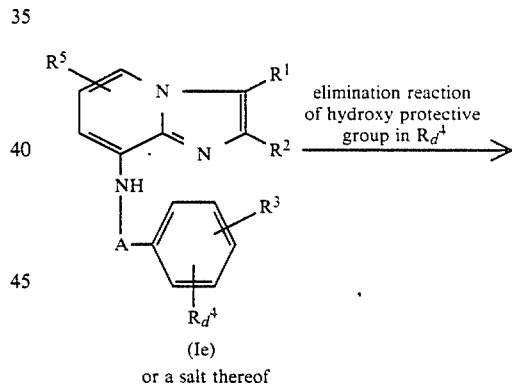
(Ie)
or a salt thereof
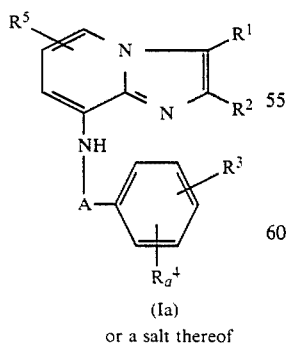
(Ia)
or a salt thereof
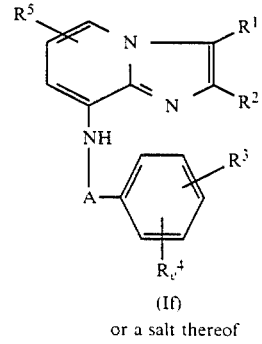
(If)
or a salt thereof
Process 5
Process 7

-continued

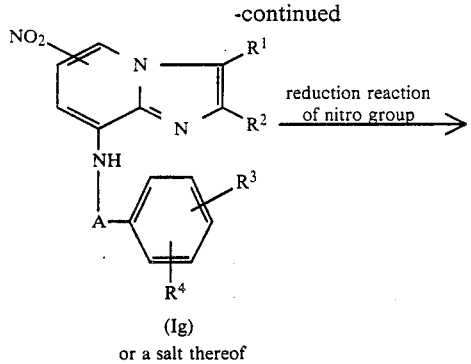

(Ig)
or a salt thereof

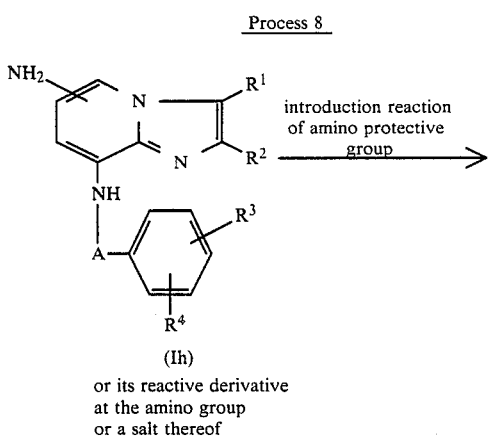

(Ih)
or a salt thereof

Process 8

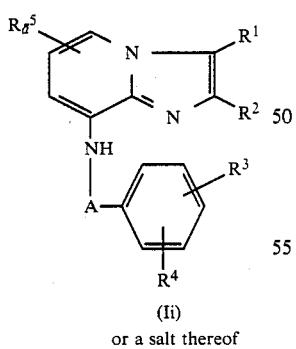

(Ih)
or its reactive derivative
at the amino group
or a salt thereof introduction reaction
of amino protective
group
⟶

(Ii)
or a salt thereof wherein
R¹, R², R³, R⁴, R⁵ and A are each as defined above,
$R_a^4$ is a protected amino,
$R_b^4$ is aroylthioureido,
$R_c^4$ is thioureido,
$R_d^4$ is protected hydroxy (lower) alkanoylamino,
$R_e^4$ is hydroxy (lower) alkanoylamino, and
$R_a^5$ is a protected amino, and X¹ and X² are each an acid residue.

The starting compounds (II) and (IV) can be prepared by the following processes.

Process A

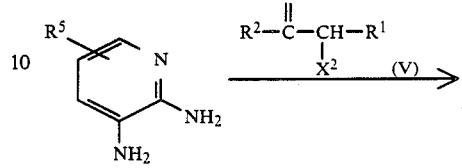

(VI)
or a salt thereof

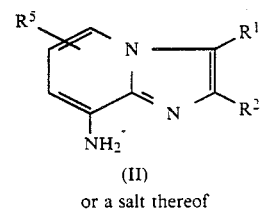

(II)
or a salt thereof

Process B

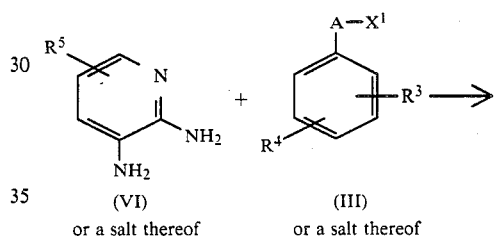

(VI)
or a salt thereof (III)
or a salt thereof

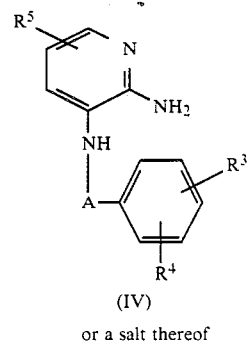

(IV)
or a salt thereof wherein R¹, R², R³, R⁴, R⁵, A, X¹ and X² are each as defined above.

The starting compound (III) or a salt thereof can be prepared by the methods described in Preparations disclosed later in the specification.

Suitable pharmaceutically acceptable salts of the object compound (I) are conventional non-toxic salts and include an organic acid salt (e.g. acetate, maleate, tartrate, methanesulfonate, benzenesulfonate, formate, toluenesulfonate, etc.), an inorganic acid salt (e.g. hydrochloride, hydrobromide, sulfate, phosphate, etc.), a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "lower alkynyl" may include ethynyl, 1-propynyl, 2-propynyl, 2-butynyl, 1-methyl-2-propynyl, 4-pentynyl, 1,1-dimethyl-2-propynyl, 1-hexynyl, 3-hexynyl and the like, in which the preferred one may be ($C_2$–$C_4$)alkynyl and the most preferred one may be 2-propynyl.

Suitable "lower alkyl" may include methyl, ethyl, propyl, isopropyl, butyl, t-butyl, pentyl, hexyl and the like, in which the preferred one may be ($C_1$–$C_4$)alkyl and the most preferred one may be methyl.

Said "lower alkyl" may have suitable substituent(s) such as halogen (e.g. fluoro, chloro, bormo, iodo) or the like, and suitable examples of "lower alkyl having suitable substituent(s)" may be mono(or di or tri)halo(lower)alkyl such as fluoromethyl, chloromethyl, difluoromethyl, trifluoromethyl, 2-fluoro-2-bromoethyl, 3-chloro-2-bromopropyl, 1-fluoromethyl-1-diiodomethylethyl, 4-bromo-3-fluoro-2-chloropentyl, 6-fluorohexyl or the like, in which the preferred one may be trihalo($C_1$–$C_4$)alkyl and the more preferred one may be trifluoromethyl.

Suitable "lower alkylene" may include methylene, ethylene, trimethylene, propylene, tetramethylene, ethylethylene, pentamethylene, hexamethylene and the like, in which the preferred one may be ($C_1$–$C_4$)alkylene and the most preferred one may be methylene.

Suitable "a protected amino" may include an amino group substituted by a conventional amino-protective group which is used in peptide chemistry, for example, ar(lower)alkyl such as mono(or di or tri)-phenyl(lower)alkyl (e.g. benzyl, benzhydryl, trityl, phenethyl, etc.) and acyl as mentioned below.

Suitable "acyl" may include carbamoyl, thiocarbamoyl, sulfamoyl, an aliphatic acyl, an aromatic acyl, a heterocyclic acyl and an aliphatic acyl substituted with aromatic or heterocyclic group(s) derived from carbamic, sulfonic, carboxylic or carbonic acids and their thio acids.

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.,), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, isopropoxycarbonyl, butoxycrbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. cyclohexanecarbonyl, etc.), lower alkoxalyl (e.g. methoxalyl, ethoxalyl, etc.), lower alkanoylcarbonyl (e.g. pyruvoyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclic carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with suitable substituent(s) such as hydroxy, amino, carboxy, lower alkyl (e.g. methyl, ethyl, propyl, isopropyl, butyl, pentyl, hexyl, etc.), halogen (e.g. chloride, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro, protected amino in which the amino protective moiety may be the same as those herein, aryl (e.g. phenyl, etc.), aroyl (e.g. benzoyl, etc.), aryloxy (e.g. benzyloxy, tolyloxy, etc.), protected hydroxy such as acyloxy, for example, lower alkanoyloxy (e.g. formyloxy, acetyloxy, propionyloxy, butyryloxy, isobutyryloxy, valeryloxy, isovaleryloxy, pivaoyloxy, hexanoyloxy, etc.), lower alkylamino (e.g. methylamino, ethylamino, etc.), and the like, and the preferable acyl having such substituent(s) may be mono (or di or tri)-halo(lower)alkanoyl (e.g., chloroacetyl, bromoacetyl, dichloroacetyl, trifluoroacetyl, etc.), amino(lower)alkanoyl (e.g., glycyl, aminopropionyl, diaminobutyryl, etc.), phenyl(lower)alkoxycarbonylamino(lower)alkanoyl (e.g., benzyloxycarbonylglycyl, etc.), lower alkanoyloxy(lower)alkanoyl (e.g., acetoxyacetyl, 2- or 3-acetoxypropionyl, etc.), lower alkylcarbamoyl (e.g. methylcarbamoyl, ethylcarbamoyl, etc.), lower alkoxycarbonylamino(lower)alkanoyl (e.g. t-butoxycarbonylaminoacetyl, etc.), phenyl(lower)alkoxycarbonylcarbamoyl (e.g. benzyloxycarbonylcarbamoyl)phenyl(lower)alkoxy(lower)alkanoyl (e.g. benzyloxyacetyl, benzyloxypropionyl, etc.), carboxy(lower)alkanoyl (e.g. carboxyacetyl, carboxypropionyl, etc.), hydroxy(lower)alkanoyl (e.g. hydroxyacetyl, hydroxypropionyl, hydroxybutyryl, etc.), aroylthiocarbamoyl (e.g. benzoylthiocarbamoyl, etc.), etc.

In said "a protected amino", the preferred one may be lower alkanoylamino, protected hydroxy(lower)alkanoylamino, hydroxy(lower)alkanoylamino, lower alkoxycarbonylamino, ureido, lower alkylureido, thioureido or aroylthioureido, in which the more preferred one may be ($C_1$–$C_4$)alkanoylamino, ($C_1$–$C_4$)alkanoyloxy($C_1$–$C_4$)alkanoylamino, hydroxy($C_1$–$C_4$)alkanoylamino, ($C_1$–$C_4$)alkoxycarbonylamino, ureido, 3-($C_1$–$C_4$)alkylureido, thioureido or 3-benzoylthioureido and the most preferred one may be formylamino, acetylamino, propionylamino, 2-acetoxyacetylamino, 2-acetoxypropionylamino, 2-hydroxyacetylamino, 2-hydroxypropionylamino, methoxycarbonylamino, ethoxycarbonylamino, t-butoxycarbonylamino, ureido, 3-methylureido, thioureido or 3-benzoylthioureido.

Suitable "a protected carboxy" may include an esterified carboxy group.

Suitable examples of the ester moiety of an "esterified carboxy" may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxypehnyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

The preferred examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, etc.), in which the more preferred one may be ($C_1$–$C_4$)alkoxycarbonyl and the most preferred one may be methoxycarbonyl.

Suitable "N,N-di(lower)alkylsulfamoyl" may include N,N-dimethylsulfamoyl, N-methyl-N-ethylsulfamoyl, N,N-dipropylsulfamoyl, N-t-butyl-N-pentylsulfamoyl, N,N-dihexylsulfamoyl and the like, in which the preferred one may be N,N-di($C_1$–$C_4$)alkyl-sulfamoyl and the more preferred one may be N,N-dimethylsulfamoyl.

Suitable "halogen" may include fluoro, chloro, bromo and iodo.

Suitable "an acid residue" may include halogen as mentioned above, acyloxy (e.g. acetoxy, tosyloxy, mesyloxy, etc.) and the like.

The processes for preparing the object compounds of the present invention are explained in detail in the following.

PROCESS 1

The object compound (I) or a salt thereof can be prepared by reacting the compound (II) or a salt thereof with the compound (III) or a salt thereof.

Suitable salts of the compound (II) and (III) can be referred to the salts as exemplified for the compound (I).

This reaction is usually carried out in a solvent such as alcohol [e.g. methanol, ethanol, etc.], benzene, N,N-dimethylformamide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

PROCESS 2

The object compound (I) or a salt thereof can be prepared by reacting the compound (IV) or a salt thereof with the compound (V).

Suitable salts of the compound (IV) can be referred to the salt as exemplified for the compound (I).

This reaction is usually carried out in a solvent such as alcohol [e.g. methanol, ethanol, etc.], benzene, N,N-dimethylformamide, tetrahydrofuran, chloroform, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate etc.], tri(lower)alkylamine [e.g. trimethylamine, triethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

PROCESS 3

The object compound (Ib) or a salt thereof can be prepared by subjecting the compound (Ia) or a salt thereof to elimination reaction of amino protective group in $R_a^4$.

Suitable salts of the compounds (Ia) and (Ib) can be referred to the salts as exemplified for the compound (I).

Suitable method for this elimination reaction may include conventional one such as hydrolysis, or the like. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,2]-octane, 1,5-diazabicyclo[5,4,0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent (e.g. methanol, ethanol, tetrahydrofuran, etc.), water or a mixed solvent thereof.

The reaction temperature is not critical, and it may suitable be selected in accordance with the kind of the amino protective group and the elimination method.

PROCESS 4

The object compound (Ia) or a salt thereof can be prepared by subjecting the compound (Ib) or its reactive derivative at the amino group or a salt thereof to introduction reaction of amino protective group.

Suitable reactive derivative at the amino group of the compound (Ib) may include Schiff's base type imino or its tautomeric enamine type isomer formed by the reaction of the compound (Ib) with a carbonyl compound such as aldehyde, ketone or the like; a silyl derivative formed by the reaction of the compound (Ib) with a silyl compound such as bis(trimethylsilyl)acetamide, mono(-trimethylsilyl)acetamide or the like; a derivative formed by reaction of the compound (Ib) with phosphorus trichloride or phosgene, and the like.

Suitable introducing agent to be used in the present reaction may include conventional one and can be shown by the formula:

$$R^6-OH \qquad (VII)$$

(wherein $R^6$ is acyl as exemplified above) or its reactive derivative or a salt thereof or isocyanate or isothiocyanate derivative (e.g. methyl isocyanate, benzoyl isothiocyanate, etc.).

Suitable salts of the compound (VII) may include an acid addition salt such as an organic acid salt (e.g. acetate, maleate, tartrate, methanesulfonate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative of the compound (VII) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, thriazole or tetrazole; or an activated ester (e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (VII) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be sued in a mixture with water.

When the compound (VII) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis(2-methylimidazole); pentamethyleneketene-N-cyclohexylimine, diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl, chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling or at room temperature.

PROCESS 5

The object compound (Id) or a salt thereof can be prepared by subjecting the compound (Ic) or a salt thereof to elimination reaction of aroyl group in $R_b{}^4$.

Suitable salts of the compounds (Ic) and (Id) can be referred to the ones as exemplified for the object compound (I).

This elimination reaction can be carried out according to a similar manner to that of Process 3.

PROCESS 6

The object compound (If) or a salt thereof can be prepared by subjecting the compound (Ie) or a salt thereof to elimination reaction of hydroxy protective group in $R_d{}^4$.

Suitalbe salts of the compounds (Ie) and (If) can be referred to the ones as exemplified for the object compound (I).

The elimination reaction of this process can be carried out according to a similar manner to the elimination reaction of Process 3.

PROCESS 7

The object compound (Ih) or a salt thereof can be prepared by subjecting a compound (Ig) or a salt thereof to reduction reaction of nitro group.

The reduction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, etc.], borane, diborane, aluminum halide [e.g. aluminum chloride, etc.], phosphorus trihalide [e.g. phosphorus trichloride, phosphorus tribromide, etc.], ferrous oxalate, a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, ammonium chloride, etc.] or the like.

Suitable catalysts to be used in catalytic reduction are conventional ones such as platinum catalyst [e.g. platinum plate, spongy platinum, platinum back, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nikel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction of this process is usually carried out in a solvent such as water, alcohol [e.g. methanol, ethanol, propanol, etc.], acetic acid, diethyl ether, dioxane, tetrahydrofuran, methylene chloride, chloroform, N,N-dimethylformamide, dimethylsulfoxide, or any other organic solvent which does not adversely influence the reaction, or a mixture thereof.

The reaction is preferably carried out under somewhat milder conditions such as under cooling to heating.

PROCESS 8

The object compound (Ii) or a salt thereof can be prepared by subjecting the compound (Ih) or its reactive derivative at the amino group or a salt thereof to introduction reaction of amino protective group.

Suitable salt of the compound (Ii) can be referred to the ones as exemplified for the compound (I).

The introduction reaction of this process can be carried out according to a similar manner to that of

PROCESS 4

The process for preparing the starting compounds are explained in detail in the following.

PROCESS A

The compound (II) or a salt thereof can be prepared by reacting the compound (VI) or a salt thereof with the compound (V).

Suitable salt of the compound (VI) can be referred to the ones as exemplified for the compound (I).

This reaction can be carried out according to a similar manner to that of Process 2 as explained before.

PROCESS B

The compound (IV) or a salt thereof can be prepared by reacting the compound (VI) or a salt thereof with the compound (III) or a salt thereof.

This reaction can be carried out according to a similar manner to that of Process 1 as explained before.

In order to illustrate the usefulness of the object compound (I), the pharmacological data of the representative compound of the object compound (I) are shown in the following.

(A)

INHIBITION ON STRESS ULCER

Test Method:

Five Sprague-Dawley rats weighing about 200 g were used per group. Each animal was immobilized in a small cage and put in a water bath allowing to respire. The temperature of the water bath kept at 22° C. The test compound was administered orally just before the immobilization. Seven hours later, the animals were sacrificed and their stomachs were removed. The stomach was then fixed with 2% formalin. The area of ulcers was measured for each animal. The mean area ($mm^2$) in the medicated animals was compared with that in the control animals.

Test Compound:

(1) 8-(2-Methyl-6-methoxycarbonylaminobenzylamino)-3-(2-propynyl)-2-methylimidazo[1,2-a]pyridine Test Result:

Inhibition % at the dose of 32 mg/kg:

| Test Compound | Inhibition % |
| --- | --- |
| (1) | 100 |

(B)

EFFECT ON GASTRIN-STIMULATED ACID SECRETION IN HEIDENHAIN POUCH DOGS

Test Method:

Dogs equipped with Heidenhain pouches were placed on tables and restrained minimally in pavlov slings. Gastrin(tetragastrin) in 0.9% saline was continuously infused through the cephalic vein at a dose of 10 μg/kg/hr over a 5- to 6-hr period in a volume of 0.1 ml/kg/min. After acid secretion had reached a plateau (usually within 2 hr), drug was given orally in a volume of 1 ml/kg. Gastric juice was collected at 15 min intervals for 1 hr before and for 3 hr after drug administration. The volume of each sample was determined, and an aliquot was titrated to pH 7.0 with 0.1M NaOH. Acid output was expressed as $\mu Eq\ H^+/15$ min. The effect of drug was described as percent drug-induced change in acid secretion.

Test Compound:

(1) 8-(2-Methyl-6-methoxycarbonylaminobenzylamino)-3-(2-propynyl)-2-methylimidazo[1,2-a]pyridine Test Result:

Maximum inhibition % at the dose of 3.2 mg/kg:

| Test Compound | Inhibiton % |
| --- | --- |
| (1) | 100 |

As being apparent from the above test results, the object compound (I) of the present invention is useful as antiulcer medicines.

For therapeutic purpose, the compounds according to the present invention can be used in a form of pharmaceutical preparation containing said compound as an active ingredient, in admixture with a pharmaceutically acceptable carrier such as an organic or inorganic solid or liquid excipient suitable for oral or parenteral administration. The pharmaceutical preparations may be capsules, tablets, dragees, solution, suspension, emulsion, and the like. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 5 mg, 10 mg, 50 mg, 100 mg, 250 mg, 500 mg, and 1000 mg of the compounds according to the present invention may be effective for treating ulcer. In general, amounts between 1 mg/body and about 2,000 mg/body or even more may be administered per day.

The following preparations and examples are given for the purpose of illustrating the present invention.

PREPARATION 1

A mixture of 2,3-diaminopyridine (62.8 g) and 3-mesyloxy-5-hexyn-2-one (109.5 g) in methanol (126 ml) was refluxed for 20 hours. After methanol was evaporated in vacuo, sodium bicarbonate aqueous solution was added to the residue and then the mixture was extracted with ethyl acetate, washed with water and sodium chloride aqueous solution, and evaporated in vacuo. The resultant residue was subjected to column chromatography on silica gel (310 g) and eluted with a mixture of methylene chloride and acetonitrile. The eluates containing the object compound were combined and evaporated in vacuo. The residue was suspended in diethyl ether and the resultant precipitates were collected by filtration to give 8-amino-3-(2-propynyl)-2-methylimidazo[1,2-a]pyridine (18.42 g).

The filtrate was evaporated and the residue was subjected to column chromatography on silica gel (120 g) again and eluted with a mixture of methylene chloride and methanol. The eluates containing the object compound were combined and evaporated in vacuo. The resultant residue was suspended in diethyl ether and the resultant precipitates were collected by filtration to give 8-amino-3-(2-propynyl)-2-methylimidazo[1,2-a]pyridine (14.10 g).

IR (Nujol): 3410, 3275, 3170, 1625, 1550 cm$^{-1}$.
NMR (CDCl$_3$, δ): 2.05 (1H, t, J=3Hz), 2.43 (3H, s), 3.72 (2H, d, J=3Hz), 4.51 (2H, broad s), 6.27 (1H, dd, J=1Hz and 7Hz), 6.63 (1H, t, J=7Hz), 7.49 (1H, dd, J=1Hz and 7Hz).

PREPARATION 2

A solution of methyl chloroformate (0.416 g) in methylene chloride (1 ml) was added dropwise to a solution of 2-amino-6-methylbenzyl alcohol (0.549 g) and pyridine (0.364 g) in methylene chloride (10 ml) with ice cooling. After being stirred for 1 hour, the mixture was poured into 1N hydrochloric acid and extracted with methylene chloride. The extract was washed with water, dried over magnesium sulfate, and evaporated in vacuo. The crystalline residue was washed with n-hexane and dried to give 2-methyl-6-methoxycarbonylaminobenzyl alcohol (0.64 g).

mp: 111° to 113° C.
IR (Nujol): 3450, 3260, 1685, 1602, 1580, 1540 cm$^{-1}$.
NMR (CDCl$_3$, δ): 2.36 (3H, s), 2.46 (1H, t, J=6Hz), 3.73 (3H, s), 4.67 (2H, d, J=6Hz), 6.87 (1H, d, J=7.5Hz), 7.11 (1H, t, J=7.5Hz), 7.47 (1H, d, J=7.5Hz), 7.40–7.70 (1H, broad s).

PREPARATION 3

To a suspension of 2-amino-6-methylbenzyl alcohol (30 g) in methylene chloride (300 ml) was added dropwise acetic anhydride (22.3 g) at 5° to 10° C. After being stirred for 3 hours, the mixture was neutralized with sodium bicarbonate aqueous solution to give precipitates. To said mixture was added chloroform to dissolve said precipitates and then the organic layer was washed with water and sodium chloride aqueous solution, dried over magnesium sulfate and evaporated in vacuo. The resultant residue was suspended in diethyl ether and the precipitates were collected by filtration to give 2-methyl-6-acetamidobenzyl alcohol (25.30 g).

mp: 118°–119° C.
IR (Nujol): 3360, 3280, 1645, 1600, 1530 cm$^{-1}$.
NMR (DMSO-d$_6$, δ): 2.07 (3H, s), 2.37 (3H, s), 4.50 (2H, s), 6.87–7.47 (3H, m), 9.33 (1H, broad s).

PREPARATION 4

A solution of potassium cyanate (1.62 g) in water (5 ml) was added dropwise to a mixture of 2-amino-6-methylbenzyl alcohol (1.37 g), water (5 ml), and acetic acid (6 ml) at room temperature. After being stirred for 2.5 hours, the resulting precipitates were collected by filtration, washed with water, and dried to give 2-methyl-6-ureidobenzyl alcohol (1.33 g).

mp: 161° to 163° C. (dec.) (recrystallized from ethanol).
IR (Nujol): 3350, 3270, 1655, 1590, 1530, 1000 cm$^{-1}$.
NMR (DMSO-d$_6$, δ): 2.32 (3H, s), 4.45 (2H, d, J=5Hz), 4.93 (1H, d, J=5Hz), 6.08 (2H, broad s), 6.82 (1H, d, J=8Hz), 7.05 (1H, t, J=8Hz), 7.55 (1H, d, J=8Hz), 7.93 (1H, s).

PREPARATION 5

To a suspension of 2-methyl-6-methoxycarbonylaminobenzyl alcohol (29.19 g) in methylene chloride (290 ml) was added dropwise thionyl chloride (11.46 ml) at room temperature and the resultant mixture was stirred for 2 hours. After the solvent was evaporated in vacuo, n-hexane was added to the residue to give precipitates. The precipitates were collected by filtration and dried to give 2-methyl-6-methoxycarbonylaminobenzyl chloride (28.26 g).

IR (Nujol): 3975, 1680, 1595, 1580, 1520 cm$^{-1}$.
NMR (CDCl$_3$, δ): 2.42 (3H, s), 3.78 (3H, s), 4.65 (2H, s), 6.55–7.00 (1H, broad s), 7.00 (1H, dd, J=2Hz and 7.5Hz), 7.25 (1H, t, J=7.5Hz), 7.60 (1H, dd, J=7.5Hz).

PREPARATION 6

To a suspension of 2-methyl-6-acetamidobenzyl alcohol (30 g) and triethylamine (46.54 ml) in methylene chloride (300 ml) was added dropwise mesyl chloride (14.25 ml) below 8° C. The mixture was stirred under ice cooling for 30 minutes and then at room temperature for 20 minutes. The reaction mixture was washed with 1N-hydrochloric acid solution, water and saturated sodium bicarbonate aqueous solution, dried over magnesium sulfate and evaporated in vacuo. The residue was suspended in n-hexane and the precipitates were collected by filtration and dried to give 2-methyl-6-acetamidobenzyl chloride (19.28 g).

IR (Nujol): 3360, 1650, 1600, 1530 cm$^{-1}$.
NMR (CDCl$_3$, δ): 2.07 (3H, s), 2.40 (3H, s), 4.80 (2H, s), 7.00–7.40 (3H, m), 9.53 (1H, broad s).

PREPARATION 7

A mixture of 2-methyl-6-ureidobenzyl alcohol (1 g) and thionyl chloride (0.66 g) in methylene chloride (20 ml) was stirred for 2 hours at room temperature and evaporated in vacuo. The residue was washed with water and dried in a desiccator to give 2-methyl-6-ureidobenzyl chloride (0.66 g).

IR (Nujol): 3250, 1650, 1540 cm$^{-1}$.
NMR (DMSO-d$_6$, δ): 4.83 (2H, s).

EXAMPLE 1

To a solution of 8-amino-3-(2-propynyl)-2-methylimidazo[1,2-a]pyridine (8.0 g) and triethylamine (4.8 g) in methanol (80 ml) was added 2-methyl-6-methoxycarbonylaminobenzyl chloride (10.15 g) and the mixture was stirred at room temperature for 17 hours. After methanol was evaporated in vacuo, the resultant residue was dissolved in methylene chloride (100 ml) and the mixture was washed with water and dried over magnesium sulfate. The solvent was evaporated in vacuo. The resultant residue was subjected to column chromatography on silica gel (240 g) and eluted with a mixture of chloroform and ethyl acetate (20:1) to give a crystalline product. The crystals were recrystallized from a mixture of ethyl acetate and n-hexane to give 8-(2-methyl-6-methoxycarbonylaminobenzylamino)-3-(2-propynyl)-2-methylimidazo[1,2-a]pyridine (6.08 g).

mp: 149° to 150° C.

IR (Nujol): 3370, 3290, 1730, 1610, 1590, 1560, 1540 cm$^{-1}$.

NMR (CDCl$_3$, δ): 2.06 (1H, t, J=3Hz), 2.36 (6H, s), 3.66 (3H, s), 3.73 (2H, d, J=3Hz), 4.35 (2H, d, J=4.5Hz), 4.85 (1H, broad t, J=4.5Hz), 6.35 (1H, d, J=7Hz), 6.76 (1H, t, J=7Hz), 6.98 (1H, d, J=7Hz), 7.25 (1H, t, J=7Hz), 7.43–7.85 (3H, m).

Analysis Calcd. for C$_{21}$H$_{22}$N$_4$O$_2$: C 69.57, H 6.18, N 15.46. Found: C 69.75, H 6.09, N 15.48.

EXAMPLE 2

To a solution of 8-amino-3-(2-propynyl)-2-methylimidazo[1,2-a]pyridine (10 g) and triethylamine (5.45 g) in methanol (100 ml) was added 2-methyl-6-acetamidobenzyl chloride (10.67 g) at room temperature and the mixture was stirred at the same temperature for 17 hours. After methanol was evaporated in vacuo, the residue was dissolved in chloroform and said solution was washed with water, dried over magnesium sulfate and evaporated in vacuo. The resultant residue was subjected to column chromatography on silica gel (350 g) and eluted with a mixture of chloroform and acetonitrile. The eluates containing the object compound were combined and evaporated in vacuo. The resultant residue (8.57 g) was subjected to column chromatography on silica gel (180 g) again and eluted with a mixture of chloroform and acetonitrile. The eluates containing the object compound were combined and evaporated in vacuo. The residue was crystallized from diethyl ether and the crystals were collected by filtration to give crude 8-(2-methyl-6-acetamidobenzylamino)-3-(2-propynyl)-2-methylimidazo[1,2-a]pyridine (6.65 g). This crude product was recrystallized from ethyl acetate (15 ml) to give pure product (5.54 g).

mp: 163°–164° C.

IR (Nujol): 3370, 3290, 3220, 3125, 1637, 1555 cm$^{-1}$.

NMR (CDCl$_3$, δ): 2.03 (3H, s), 2.06 (1H, t, J=3Hz), 2.39 (6H, s), 3.76 (2H, d, J=3Hz), 4.37 (2H, d, J=5Hz), 4.91 (1H, broad t, J=5Hz), 6.37 (1H, d, J=7Hz), 6.80 (1H, t, J=7Hz), 6.95–7.42 (2H, m), 7.52–7.86 (2H, m), 8.18 (1H, broad s).

Analysis Calcd. for C$_{21}$H$_{22}$N$_4$O: C 72.60, H 6.38, N 16.13. Found: C 72.84, H 6.44, N 15.99.

PREPARATION 8

8-Amino-3-(2-propynyl)-2,6-dimethylimidazo[1,2-a]pyridine was obtained by reacting 2,3-diamino-5-methylpyridine with 3-mesyloxy-5-hexyn-2-one according to a similar manner to that of Preparation 1.

mp: 155° to 159° C.

IR (Nujol): 3425, 3280, 3170, 3120, 1615, 1555, 1530 cm$^{-1}$.

NMR (CDCl$_3$, δ): 2.03 (1H, t, J=3Hz), 2.23 (3H, s), 2.40 (3H, s), 3.68 (2H, d, J=3Hz), 4.37 (2H, broad s), 6.17 (1H, s), 7.27 (1H, s).

PREPARATION 9

8-Amino-3-(2-propynyl)-2,5-dimethylimidazo[1,2-a]pyridine was obtained by reacting 2,3-diamino-6-methylpyridine with 3-mesyloxy-5-hexyn-2-one according to a similar manner to that of Preparation 1.

mp: 112° to 116° C.

IR (Nujol): 3425, 3300, 3210, 1620, 1560, 1510 cm$^{-1}$.

NMR (CDCl$_3$, δ): 2.13 (1H, t, J=3Hz), 2.40 (3H, s), 2.83 (3H, s), 3.88 (2H, d, J=3Hz), 4.30 (2H, broad s), 6.20 (2H, broad s).

PREPARATION 10

8-Amino-3-(2-propynyl)-2,7-dimethylimidazo[1,2-a]pyridine was obtained by reacting 2,3-diamino-4-methylpyridine with 3-mesyloxy-5-hexyn-2-one according to a similar manner to that of Preparation 1.

mp: 84° to 86° C.

IR (Nujol): 3400, 3320, 3290, 3210, 2100, 1610, 1575, 1530 cm$^{-1}$.

NMR (CDCl$_3$, δ): 2.02 (1H, t, J=3Hz), 2.19 (3H, s), 2.40 (3H, s), 3.70 (2H, d, J=3Hz), 3.40–4.70 (2H, broad), 6.51 (1H, d, J=7Hz), 7.43 (1H, d, J=7Hz).

Mass: 199 (M+).

PREPARATION 11

8-Amino-6-chloro-3-(2-propynyl)-2-methylimidazo[1,2-a]pyridine was obtained by reacting 2,3-diamino-5-chloropyridine with 3-mesyloxy-5-hexyn-2-one according to a similar manner to that of Preparation 1.

mp: 161° to 163° C.

IR (Nujol): 3450, 3310, 3225, 1615, 1545 cm$^{-1}$.

NMR (CDCl$_3$, δ): 2.07 (1H, t, J=3Hz), 2.40 (3H, s), 3.68 (2H, d, J=3Hz), 4.57 (2H, broad s), 6.28 (1H, d, J=2Hz), 7.52 (1H, d, J=2Hz).

PREPARATION 12

2-Methyl-6-ethoxycarbonylaminobenzyl alcohol was obtained according to a similar manner to that of Preparation 2.

mp: 58° to 59° C. (recrystallized from n-hexane).

IR (Nujol): 3415, 3320, 1695, 1685, 1620, 1600 cm$^{-1}$.

NMR (CDCl$_3$, δ): 1.30 (3H, t, J=7Hz), 2.36 (3H, s), 2.30–2.70 (1H, broad s), 4.21 (2H, q, J=7Hz), 4.70 (2H, s), 6.93 (1H, b, dd, J=2Hz and 8Hz), 7.19 (1H, t, J=8Hz), 7.55 (1H, b, dd, J=2Hz and 8Hz), 7.50–7.80 (1H, broad s).

PREPARATION 13

2-Methyl-6-t-butoxycarbonylaminobenzyl alcohol was obtained according to a similar manner to that of Preparation 3.

mp: 96° to 98° C.

IR (Nujol): 3450, 3320, 1695, 1600, 1580, 1520 cm$^{-1}$.

NMR (CDCl$_3$, δ): 1.50 (9H, s), 2.40 (2H, s), 4.73 (2H, d, J=6Hz), 6.80–7.63 (4H, m).

PREPARATION 14

2-Methyl-6-ethoxycarbonylaminobenzyl chloride was obtained according to a similar manner to that of Preparation 5.

mp: 112° to 113° C.

IR (Nujol): 3260, 1680, 1590, 1580, 1520 cm$^{-1}$.

NMR (CDCl$_3$, δ): 1.31 (3H, t, J=7Hz), 2.41 (3H, s), 4.25 (2H, q, J=7Hz), 4.66 (2H, s), 6.75 (1H, broad s), 7.01 (1H, d, J=8Hz), 7.25 (1H, t, J=8Hz), 7.62 (1H, d, J=8Hz).

PREPARATION 15

2-Methyl-6-t-butoxycarbonylaminobenzyl chloride was obtained according to a similar manner to that of Preparation 6.

mp: 75° to 76° C.

IR (Nujol): 3355, 1685, 1600, 1582, 1510 cm$^{-1}$.

NMR (CDCl$_3$, δ): 1.52 (9H, s), 2.42 (3H, s), 4.67 (2H, s), 6.60 (1H, broad s), 7.0 (1H, d, J=7.5Hz), 7.40 (1H, t, J=7.5Hz), 7.80 (1H, d, J=7.5Hz).

PREPARATION 16

To a solution of 2,3-diaminopyridine (1.09 g) in methanol (22 ml) was added 2-methyl-6-methoxycarbonylaminobenzyl chloride (2.14 g) and potassium carbonate (1.38 g) at room temperature and the mixture was stirred for 1.5 hours. The insoluble material was removed by filtration and methanol in the filtrate was evaporated under reduced pressure. The residue was subjected to column chromatography on silica gel (30 g) and eluted with a mixture of chloroform and methanol (100:1) to give a crystalline product. The crystals were triturated with diisopropyl ether to give 2-amino-3-(2-methyl-6-methoxycarbonylaminobenzylamino)-pyridine (1.44 g).

mp: 176° to 178° C.

IR (Nujol): 3445, 3290, 3125, 1730, 1645, 1590 cm$^{-1}$.

NMR (DMSO-d$_6$, δ): 2.33 (3H, s), 3.58 (3H, s), 4.08 (2H, d, J=5Hz), 4.52 (1H, t, J=5Hz), 5.40 (2H, s), 6.37–6.57 (1H, m), 6.67–6.82 (1H, m), 6.90–7.40 (4H, m), 8.77 (1H, s).

PREPARATION 17

2-Amino-3-(2-methyl-6-methoxycarbonylaminobenzylamino)-5-trifluoromethylpyridine was obtained by reacting 2,3-diamino-5-trifluoromethylpyridine with 2-methyl-6-methoxycarbonylaminobenzyl chloride according to a similar manner to that of Preparation 16.

mp: 157° to 159° C.

IR (Nujol): 3420, 3350, 3200, 1730, 1660, 1600, 1580, 1520 cm$^{-1}$.

NMR (DMSO-d$_6$, δ): 2.33 (3H, s), 3.58 (3H, s), 4.13 (2H, d, J=5Hz), 4.93 (1H, t, J=5Hz), 6.28 (2H, broad s), 6.78 (1H, broad s), 6.92–7.42 (3H, m), 7.60 (1H, broad s), 8.80 (1H, s).

PREPARATION 18

2-Amino-3-(2-methyl-6-methoxycarbonylaminobenzylamino)-5-methoxycarbonylpyridine was obtained by reacting 2,3-diamino-5-methoxycarbonylpyridine with 2-methyl-6-methoxycarbonylaminobenzyl chloride according to a similar manner to that of Preparation 16.

mp: 194° to 197° C.

IR (Nujol): 3430, 3320, 3125, 1705, 1680, 1590, 1525 cm$^{-1}$.

NMR (DMSO-d$_6$, δ): 2.33 (3H, s), 3.58 (3H, s), 3.76 (3H, s), 4.13 (2H, d, J=5Hz), 4.73 (1H, t, J=5Hz), 6.40 (2H, broad s), 6.90–7.40 (4H, m), 7.98 (1H, d, J=2Hz), 8.80 (1H, s).

PREPARATION 19

2-Amino-3-(2-methyl-6-methoxycarbonylaminobenzylamino)-6-chloropyridine was obtained by reacting 2,3-diamino-6-chloropyridine and 2-methyl-6-methoxycarbonylaminobenzyl chloride according to a similar manner to that of Preparation 16.

mp: 179° to 182° C.

IR (Nujol): 3450, 3250, 3170, 1702, 1620, 1600, 1580, 1523 cm$^{-1}$.

NMR (DMSO-d$_6$, δ): 2.30 (3H, s), 3.57 (3H, s), 4.07 (2H, d, J=5Hz), 4.62 (1H, t, J=5Hz), 5.90 (2H, broad s), 6.43 (1H, d, J=8Hz), 6.72 (1H, d, J=8Hz), 6.90–7.40 (3H, m), 8.77 (1H, s).

PREPARATION 20

2-Amino-3-(2-methyl-6-methoxycarbonylaminobenzylamino)-6-acetamidopyridine was obtained by reacting 2,3-diamino-6-acetamidopyridine with 2-methyl-6-methoxycarbonylaminobenzyl chloride according to a similar manner to that of Preparation 16.

mp: 215° to 216° C.

IR (Nujol): 3440, 3350, 3250, 3200, 1703, 1685, 1640, 1605, 1590, 1520 cm$^{-1}$.

NMR (DMSO-d$_6$, δ): 2.02 (3H, s), 2.37 (3H, s), 3.63 (3H, s), 4.10 (2H, d, J=5Hz), 4.38 (1H, t, J=5Hz), 5.38 (2H, broad s), 6.65–7.47 (5H, m), 8.73 (1H, s), 9.52 (1H, s).

PREPARATION 21

2-Amino-3-(2-methyl-6-methoxycarbonylaminobenzylamino)-5-nitropyridine was obtained by reacting 2,3-diamino-5-nitropyridine with 2-methyl-6-methoxycarbonylaminobenzyl chloride according to a similar manner to that of Preparation 16.

mp: 181° to 183° C.

IR (Nujol): 3410, 3320, 1720, 1655, 1590, 1520 cm$^{-1}$.

NMR (DMSO-d$_6$, δ): 2.33 (3H, s), 3.57 (3H, s), 4.18 (2H, d, J=5Hz), 5.12 (1H, t, J=3Hz), 6.90–7.37 (6H, m), 8.28 (1H, d, J=2Hz), 8.80 (1H, s).

PREPARATION 22

To a solution of 2,3-diaminopyridine (546 mg) and 2-methyl-6-methoxycarbonylaminobenzaldehyde (966 mg)*, which was prepared by reacting 2-methyl-6-aminobenzaldehyde with methyl chloroformate according to a similar manner to that of Preparation 2, and triethylamine (2.5 g) in methylene chloride (26 ml) was added a 0.5M solution of titanium tetrachloride in methylene chloride (6 ml) at 0° C. and the mixture was stirred for 2 hours at the same temperature. To the mixture, water was added and the insoluble materials were removed by filtration, and the organic layer was separated. The solvent was evaporated under reduced pressure. The residue was subjected to column chromatography on silica gel (27 g), eluting with a mixture of chloroform and methanol (50:1). The fractions containing the desired product were combined and the solvent was removed under reduced pressure. The residue was triturated with diethyl ether to give 2-amino-3-(2-methyl-6-methoxycarbonylaminobenzylideneamino)pyridine (279 mg).

mp: 198° to 200° C.

IR (Nujol): 3480, 3280, 3125, 1728, 1615, 1595, 1570 cm$^{-1}$.

NMR (CDCl₃, δ): 2.56 (3H, s), 3.78 (3H, s), 5.06 (2H, broad s), 6.67 (1H, dd, J=5Hz and 8Hz), 6.85 (1H, d, J=8Hz), 7.23 (1H, dd, J=2Hz and 8Hz), 7.31 (1H, t, J=8Hz), 7.94 (1H, dd, J=2Hz and 5Hz), 8.25 (1H, d, J=8Hz), 8.93 (1H, s), 12.36 (1H, broad s).

* Physical data of 2-methyl-6-methoxycarbonylaminobenzaldehyde were as follows.
mp: 88° to 89° C.
IR (Nujol): 1730, 1660, 1640, 1605, 1580, 1520 cm⁻¹.
NMR (CDCl₃, δ): 2.65 (3H, s), 3.80 (3H, s), 6.89 (1H, d, J=8Hz), 7.47 (1H, t, J=8Hz), 8.36 (1H, d, J=8Hz), 10.36 (1H, s), 11.06 (1H, broad s).

PREPARATION 23

To a solution of 2-amino-3-(2-methyl-6-methoxycarbonylaminobenzylideneamino)pyridine (229 mg) in methanol (4.6 ml) and chloroform (4.6 ml) was added sodium borohydride (200 mg) and the mixture was stirred for 3.5 hours at room temperature. After water was added, organic layer was separated and dried over magnesium chloride. The solvent was evaporated under reduced pressure. The residue was triturated with diethyl ether to give 2-amino-3-(2-methyl-6-methoxycarbonylaminobenzylamino)pyridine (217 mg).

The physical data of this compound were substantially the same as those of the compound obtained in Preparation 16.

The following compounds (Examples 3 to 26) were obtained according to a similar manner to that of Example 1 or 2.

EXAMPLE 3

8-(2-Methyl-6-ureidobenzylamino)-3-(2-propynyl)-2-methylimidazo[1,2-a]pyridine.

mp: 242°-245° C.
IR (Nujol): 3260, 1650, 1560, 1100 cm⁻¹.
NMR (DMSO-d₆, δ): 2.25 (3H, s), 2.30 (3H, s), 2.90 (1H, t, J=3Hz), 3.83 (2H, d, J=3Hz), 4.27 (2H, d, J=5Hz), 5.33 (1H, t, J=5Hz), 5.88 (2H, broad s), 6.17-6.33 (1H, m), 6.60-7.60 (5H, m), 7.90 (1H, broad s).

EXAMPLE 4

8-(2-Methyl-6-t-butoxycarbonylaminobenzylamino)-3-(2-propynyl)-2-methylimidazo[1,2-a]pyridine.

mp: 133° to 135° C.
IR (Nujol): 3350, 3310, 1705, 1550 cm⁻¹.
NMR (CDCl₃, δ): 1.46 (9H, s), 2.06 (1H, t, J=3Hz), 2.36 (3H, s), 2.40 (3H, s), 3.76 (2H, d, J=3Hz), 4.36 (2H, d, J=5Hz), 4.90 (1H, d, J=5Hz), 6.37 (1H, d, J=7Hz), 6.80 (1H, t, J=7Hz), 6.46-7.36 (4H, m), 7.53-7.76 (2H, m).

EXAMPLE 5

8-(2-Methyl-6-ethoxycarbonylaminobenzylamino)-3-(2-propynyl)-2-methylimidazo[1,2-a]pyridine.

mp: 141° to 142.5° C.
IR (Nujol): 3350, 3270, 1720, 1605, 1585, 1555, 1540 cm⁻¹.
NMR (CDCl₃, δ): 1.22 (3H, t, J=7.5Hz), 2.06 (1H, t, J=3Hz), 2.36 (3H, s), 2.38 (3H, s), 3.75 (2H, d, J=3Hz), 4.16 (2H, q, J=7.5Hz), 4.36 (2H, d, J=5Hz), 4.87 (1H, bt, J=5Hz), 6.36 (1H, d, J=7Hz), 6.70-7.46 (4H, m), 7.53-7.81 (2H, m).

Analysis calcd. for C₂₂H₂₄N₄O₂: C 70.19, H 6.43, N 14.88. Found: C 70.35, H 6.55, N 14.58.

EXAMPLE 6

8-(2-Methyl-6-methoxycarbonylaminobenzylamino)-5-methyl-3-(2-propynyl)-2-methylimidazo[1,2-a]pyridine.

mp: 95° to 97° C.
IR (Nujol): 3400, 3260, 1690, 1640, 1575, 1525 cm⁻¹.
NMR (CDCl₃, δ): 2.15 (1H, t, J=3Hz), 2.35 (6H, s), 2.87 (3H, s), 3.67 (3H, s), 3.88 (2H, d, J=3Hz), 4.27 (2H, d, J=5Hz), 4.73 (1H, t, J=5Hz), 6.18 (1H, d, J=8Hz), 6.37 (1H, d, J=8Hz), 6.92 (1H, d, J=7.5Hz), 7.18 (1H, t, J=7.5Hz), 7.60 (1H, s), 7.65 (1H, d, J=7.5Hz).

Analysis calcd. for C₂₂H₂₄N₄O₂·H₂O C 66.98, H 6.64, N 14.20. Found: C 67.56, H 6.71, N 14.16.

EXAMPLE 7

8-(2-Methyl-6-methoxycarbonylaminobenzylamino)-6-methyl-3-(2-propynyl)-2-methylimidazo[1,2-a]pyridine.

mp: 208° to 210° C.
IR (Nujol): 3240, 3040, 2590, 1702, 1662, 1585, 1520 cm⁻¹.
NMR (DMSO-d₆, δ): 2.35 (3H, s), 2.40 (3H, s), 2.43 (3H, s), 3.08 (1H, t, J=3Hz), 3.57 (3H, s), 4.02 (2H, d, J=3Hz), 4.38 (2H, d, J=5Hz), 6.77 (2H, m), 6.93-7.27 (3H, m), 7.80 (1H, s), 9.03 (1H, s).

Analysis Calcd. for C₂₂H₂₄N₄O₂·HCl C 63.99, H 6.10, N 13.57. Found: C 64.49, H 6.08, N 13.69.

EXAMPLE 8

8-(2-Methyl-6-methoxycarbonylaminobenzylamino)-7-methyl-3-(2-propynyl)-2-methylimidazo[1,2-a]pyridine.

mp: 131° to 133° C.
IR (Nujol): 3300, 1720, 1600, 1585, 1530 cm⁻¹.
NMR (CDCl₃, δ): 2.04 (1H, t, J=3Hz), 2.30 (3H, s), 2.45 (6H, s), 3.60-3.80 (6H, s), 4.67 (2H, s), 6.56 (1H, d, J=7Hz), 6.86 (1H, d, J=8Hz), 7.13 (1H, t, J=8Hz), 7.59 (1H, d, J=7Hz), 7.86 (1H, d, J=8Hz), 9.73 (1H, s).

Mass: 376 (M⁺).

EXAMPLE 9

8-(2-Methyl-6-methoxycarbonylaminobenzylamino)-6-chloro-3-(2-propynyl)-2-methylimidazo[1,2a]pyridine.

mp: 125° to 126° C.
IR (Nujol): 3380, 3260, 1685, 1570, 1525 cm⁻¹.
NMR (DMSO-d₆, δ): 2.24 (3H, s), 2.30 (3H, s), 2.93 (1H, t, J=3Hz), 3.57 (3H, s), 3.85 (2H, d, J=3Hz), 4.33 (2H, d, J=5Hz), 5.78 (1H, t, J=5Hz), 6.27 (1H, d, J=2Hz), 6.93-7.27 (3H, m), 7.68 (1H, d, J=2Hz), 9.05 (1H, s).

Analysis Calcd. for C₂₁H₂₂ClN₄O₂·½H₂O C 61.99, H 5.70, N 13.77. Found: C 61.38, H 5.65, N 13.73.

EXAMPLE 10

8-(2-Methyl-6-methoxycarbonylaminobenzylamino)-5-chloro-3-(2-propynyl)-2-methylimidazo[1,2-a]pyridine.

IR (Nujol): 3280, 3210, 3180, 2500, 1690, 1650, 1590, 1520 cm⁻¹.

EXAMPLE 11

8-(2-Methyl-6-methoxycarbonylaminobenzylamino)-5-acetamido-3-(2-propynyl)-2-methylimidazo[1,2-a]pyridine.

IR (Nujol): 3370, 3250, 1740, 1660, 1610, 1565, 1520 cm⁻¹.

EXAMPLE 12

8-(2-Methyl-6-methoxycarbonylaminobenzylamino)-6-methoxycarbonyl-3-(2-propynyl)-2-methylimidazo[1,2-a]pyridine.

IR (Nujol): 3290, 1733, 1710, 1560, 1525, 1223 cm$^{-1}$.

EXAMPLE 13

8-(2-Methyl-6-methoxycarbonylaminobenzylamino)-6-trifluoromethyl-3-(2-propynyl)-2-methylimidazo[1,2-a]pyridine.

IR (Nujol): 3360, 3230, 1730, 1600, 1565, 1530 cm$^{-1}$.

EXAMPLE 14

8-(2-Methyl-6-methoxycarbonylaminobenzylamino)-6-nitro-3-(2-propynyl)-2-methylimidazo[1,2-a]pyridine.

IR (Nujol): 3400, 3300, 3260, 1690, 1640, 1565, 1525 cm$^{-1}$.

EXAMPLE 15

8-(2-Methyl-6-methoxycarbonylaminobenzylamino)-6-(N,N-dimethylsulfamoyl)-3-(2-propynyl)-2-methylimidazo[1,2-a]pyridine.

IR (Nujol): 3400, 3300, 3250, 1690, 1550, 1515 cm$^{-1}$.

EXAMPLE 16

8-(2-Methyl-6-aminobenzylamino)-3-(2-propynyl)-2-methylimidazo[1,2-a]pyridine.

IR (Nujol): 3420, 3310, 3290, 3220, 1620, 1545 cm$^{-1}$.

EXAMPLE 17

8-(2-Methyl-6-propionylaminobenzylamino)-3-(2-propynyl)-2-methylimidazo[1,2-a]pyridine.

IR (Nujol): 3375, 3300, 3225, 1645, 1555, 1530 cm$^{-1}$.

EXAMPLE 18

8-[2-Methyl-6-(3-methylureido)benzylamino]-3-(2-propynyl)-2-methylimidazo[1,2-a]pyridine.

IR (Nujol): 3375, 3325, 3295, 3210, 2100, 1695, 1560 cm$^{-1}$.

EXAMPLE 19

8-(2-Methyl-6-formamidobenzylamino)-3-(2-propynyl)-2-methylimidazo[1,2-a]pyridine.

IR (Nujol): 3400, 3210, 1690, 1605, 1580, 1555, 1535 cm$^{-1}$.

EXAMPLE 20

8-[2-Methyl-6-(2-acetoxypropionylamino)benzylamino]-3-(2-propynyl)-2-methylimidazo[1,2-a]pyridine.

IR (Nujol): 3360, 3290, 1745, 1685, 1600, 1585, 1550, 1520 cm$^{-1}$.

EXAMPLE 21

8-[2-Methyl-6-(2-acetoxyacetyl)aminobenzylamino]-3-(2-propynyl)-2-methylimidazo[1,2-a]pyridine.

IR (Nujol): 3380, 3295, 1750, 1690, 1660, 1560, 1520 cm$^{-1}$.

EXAMPLE 22

8-[2-Methyl-6-(3-benzoylthioureido)benzylamino]-3-(2-propynyl)-2-methylimidazo[1,2-a]pyridine.

IR (Nujol): 3350, 3300, 3275, 1670, 1570, 1525 cm$^{-1}$.

EXAMPLE 23

8-(2-Methyl-6-thioureidobenzylamino)-3-(2-propynyl)-2-methylimidazo[1,2-a]pyridine.

IR (Nujol): 3400, 3325, 3280, 3125, 1635, 1558, 1515, 1500 cm$^{-1}$.

EXAMPLE 24

8-[2-Methyl-6-(2-hydroxyacetyl)aminobenzylamino]-3-(2-propynyl)-2-methylimidazo[1,2-a]pyridine.

IR (Nujol): 3375, 3220, 1690, 1590, 1560, 1520, 1500 cm$^{-1}$.

EXAMPLE 25

8-[2-Methyl-6-(2-hydroxypropionyl)aminobenzylamino]-3-(2-propynyl)-2-methylimidazo[1,2-a]pyridine.

IR (Nujol): 3390, 3330, 3300, 3100, 2110, 1680, 1580, 1560, 1520 cm$^{-1}$.

EXAMPLE 26

8-(2-Methyl-6-methoxycarbonylaminobenzylamino)-6-acetamido-3-(2-propynyl)-2-methylimidazo[1,2-a]pyridine.

IR (Nujol): 3380, 3250, 3180, 1725, 1650, 1575 cm$^{-1}$.

EXAMPLE 27

A mixture of 2-amino-3-(2-methyl-6-methoxycarbonylaminobenzylamino)pyridine (180 mg) and 3-mesyloxy-5-hexyn-2-one (120 mg) in methanol (0.36 ml) and chloroform (0.36 ml) was refluxed for 20 hours. After cooling, chloroform was added to the mixture and the resultant mixture was washed with an aqueous solution of sodium carbonate and water. The solvent was evaporated under reduced pressure and the residue was subjected to column chromatography on silica gel (4 g), eluting with chloroform to give an oily product. The residue was triturated with diethyl ether to give 8-(2-methyl-6-methoxycarbonylaminobenzylamino)-3-(2-propynyl)-2-methylimidazo[1,2-a]pyridine (127 mg).

mp: 149° to 150° C.

IR (Nujol): 3370, 3290, 1730, 1610, 1590, 1560, 1540 cm$^{-1}$.

NMR (CDCl$_3$, δ): 2.06 (1H, t, J=3Hz), 2.36 (6H, s), 3.66 (3H, s), 3.73 (2H, d, J=3Hz), 4.35 (2H, d, J=4.5Hz), 4.85 (1H, t, J=4.5Hz), 6.35 (1H, d, J=7Hz), 6.76 (1H, t, J=7Hz), 6.98 (1H, d, J=7Hz), 7.25 (1H, t, J=7Hz), 7.43–7.85 (3H, m).

The following compounds (Example 28 to 51) were obtained according to a similar manner to that of Example 27.

EXAMPLE 28

8-(2-Methyl-6-methoxycarbonylaminobenzylamino)-5-chloro-3-(2-propynyl)-2-methylimidazo[1,2-a]pyridine.

mp: 203° to 205° C. (decomp.).

IR (Nujol): 3280, 3210, 3180, 2500, 1690, 1650, 1590, 1520 cm$^{-1}$.

NMR (DMSO-d$_6$, δ): 2.37 (3H, s), 2.43 (3H, s), 3.12 (1H, t, J=3Hz), 3.58 (3H, s), 4.18 (2H, d, J=3Hz), 4.37 (2H, broad s), 6.30–7.40 (6H, m), 9.00 (1H, s).

Analysis Calcd. for C$_{21}$H$_{22}$ClN$_4$O$_2$·HCl C 58.21, H 5.11, N 12.93. Found: C 58.50, H 5.22, N 12.92.

EXAMPLE 29

8-(2-Methyl-6-methoxycarbonylaminobenzylamino)-5-acetamido-3-(2-propynyl)-2-methylimidazo[1,2-a]pyridine.

mp: 192° to 195° C. (decomp.).

IR (Nujol): 3370, 3250, 1740, 1660, 1610, 1565, 1520 cm$^{-1}$.

NMR (DMSO-d$_6$, δ): 2.08 (3H, s), 2.25 (3H, s), 2.33 (3H, s) 2.82 (1H, t, J=3 Hz), 3.60 (3H, s), 3.83 (2H, d,

J=3 Hz), 4.32 (2H, d, J=5 Hz), 5.40 (1H, t, J=5 Hz), 6.18 (1H, d, J=7.5 Hz), 6.40 (1H, d, J=7.5 Hz), 6.90–7.30 (3H, m), 9.03 (1H, s).

EXAMPLE 30

8-(2-Methyl-6-methoxycarbonylaminobenzylamino)-6-methoxycarbonyl-3-(2-propynyl)-2-methylimidazo[1,2-a]pyridine.

mp: 175° to 176° C.

IR (Nujol): 3290, 1733, 1710, 1560, 1525, 1223 cm$^{-1}$.

NMR (CDCl$_3$, δ): 2.10 (1H, t, J=3 Hz), 2.37 (6H, s), 3.68 (3H, s) 3.76 (2H, d, J=3 Hz), 3.95 (3H, s), 4.37 (2H, d, J=5 Hz), 4.59 (1H, t, J=5 Hz), 6.80–7.33 (3H, m) 6.85 (1H, d, J=2 Hz), 7.53–7.77 (1H, m), 8.32 (1H, d, J=2 Hz).

Analysis Calcd. for C$_{23}$H$_{22}$N$_4$O$_4$: C 65.66, H 5.75, N 13.32. Found: C 66.00, H 5.91, N 13.33.

EXAMPLE 31

8-(2-Methyl-6-methoxycarbonylaminobenzylamino)-6-trifluoromethyl-3-(2-propynyl)-2-methylimidazo[1,2-a]pyridine.

mp: 188° to 190° C.

IR (Nujol): 3360, 3230, 1730, 1600, 1565, 1530 cm$^{-1}$.

NMR (DMSO-d$_6$, δ): 2.30 (3H, s) 2.32 (3H, s), 2.95 (1H, t, J=3 Hz), 3.57 (3H, s), 3.95 (2H, d, J=3 Hz), 4.40 (2H, d, J=5 Hz), 5.87 (1H, t, J=5 Hz), 6.37 (1H, broad s), 6.95–7.30 (3H, m), 8.03 (1H, broad s), 9.03 (1H, s).

Analysis Calcd. for C$_{21}$H$_{22}$N$_4$O$_2$: C 61.39, H 4.92, N16.02. Found: C 61.44, H 5.58, N 12.98.

EXAMPLE 32

8-(2Methyl-6methoxycarbonylaminobenzylamino)-6-nitro-3-(2-propynyl)-2-methylimidazo[1,2-a]pyridine mp: 201° to 203° C. (decomp.).

IR (Nujol): 3400, 3300, 3260, 1690, 1640, 1565, 1525 cm$^{-1}$.

NMR (CDCl$_3$, δ): 2.13 (1H, t, J=3Hz), 2.40 (6H, s), 3.68 (3.78 (2H, d, J=3 Hz), 4.38 (2H, d, J=5 Hz), 5.25 (1H, t, J=5 Hz), 6.80–7.63 (4H, m) 6.98 (1H, d, J=2 Hz), 8.62 (1H, d, J=2Hz).

Analysis Calcd. for C$_{21}$H$_{21}$N$_5$O$_4$: C 61.91, H 5.19, N 17.19. Found: C 61.46, H 5.16, N 16.45.

EXAMPLE 33

8-(2-Methyl-6-acetamidobenzylamino)-3-(2-propynyl)-2-methylimidazo[1,2a]pyridine.

IR (Nujol): 3370, 3290, 3220, 3125, 1637, 1555 cm$^{=1}$.

EXAMPLE 34

8-(2-Methyl-6-ureidobenzylamino)-3-(2-propynl)-2-methYlimidazo[1,2-a]pyridine.

IR (Nujol): 3260, 1650, 1560, 1100 cm$^{-1}$.

EXAMPLE 35

8-(2-Methyl-6-t-butoxycarbonylaminobenzylamino)-3-(2-propynyl)-2-2-methylimidazo[1,2-a]pyridine.

IR (Nujol): 3350, 3310, 1705, 1550 cm$^{-1}$.

EXAMPLE 36

8-(2Methyl-6-ethoxycarbonylaminobenzylamino)-3-(2-propynyl)-2-methylimidazo[1,2-a]pyridine.

IR (Nujol): 3350, 3270, 1720, 1605, 1585, 1555, 1540 cm$^{-1}$.

EXAMPLE 37

8-(2-Methyl-6-methoxycarbonylaminobenzylamino)-5-methyl-3-(2-propynyl)-2-methylimidazo[1,2-a]pyridine.

IR (Nujol): 3400, 3260, 1690, 1640, 1575, 1525 cm$^{-1}$.

EXAMPLE 38

8-(2-Methyl-6-methoxycarbonylaminobenzylamino)-6-methyl-3-(2-propynyl)-2-methylimidazo[1,2-a]pyridine.

IR (Nujol): 3240, 3040, 2590, 1702, 1662, 1585, 1520 cm$^{-1}$.

EXAMPLE 39

8-(2-Methyl-6-methoxycarbonylaminobenzylamino)-7-methyl-3-(2-propynyl)-2-methylimidazo[1,2-a]pyridine.

IR (Nujol): 3300, 1720, 1600, 1585, 1530 cm$^{-1}$.

EXAMPLE 40

8-(2-Methyl-6-methoxycarbonylaminobenzylamino)-6-chloro-3-(2-propynyl)-2-methylimidazo[1,2-a]pyridine.

IR (Nujol): 3380, 3260, 1685, 1570, 1525 cm$^{-1}$.

EXAMPLE 41

8-(2-Methyl-6-aminobenzylamino)-3-(2-propynyl)-2-methylimidazo[1,2≠-a]pyridine.

IR (Nujol): 3420, 3310, 3290, 3220, 1620, 1545 cm$^{-1}$.

EXAMPLE 42

8-(2-Methyl-6-propionylaminobenzylamino)-3-(2-propynyl)-2-methylimidazo[1,2-a]pyridine.

IR (Nujol): 3375, 3300, 3225, 1645, 1555, 1530 cm$^{-1}$.

EXAMPLE 43

8-[2-Methyl-6-(3-methylureido)benzylamino]-3(2-propynyl)-2-methylimidazo[1,2-]pyridine.

IR (Nujol): 3375, 3325, 3295, 3210, 2100, 1695, 1560 cm$^{-1}$.

EXAMPLE 44

8-(2-Methyl-6-formamidobenzylamino)-3-(2-propynyl)-2-methylimidazo[1,2-a]pyridine.

IR (Nujol): 3400, 3210, 1690, 1605, 1580, 1555, 1535 cm$^{-1}$.

EXAMPLE 45

8-[2-Methyl-6-(2-acetoxypropionylamino)benzylamino]-3-(2propynyl)-2-methylimidazo[1,2-a]pyridine.

IR (Nujol): 3360, 3290, 1745, 1685, 1600, 1585, 1550, 1520 cm$^{-1}$.

EXAMPLE 46

8-[2-Methyl-6-(2-acetoxyacetyl)aminobenzylamino]-3-(2-propynyl)-2-methylimidazo[1,2-a]pyridine.

IR (Nujol): 3380, 3295, 1750, 1690, 1660, 1560, 1520 cm$^{-1}$.

EXAMPLE 47

8-[2-Methyl-6-(3-benzoylthioureido)benzylamino]-3-(2-propynyl)-2-methylimidazo[1,2-a]pyridine.

IR (Nujol): 3350, 3300, 3275, 1670, 1570, 1525 cm$^{-1}$.

EXAMPLE 48

8-(2-Methyl-6-thioureidobenzylamino)-3-(2-propynyl)-2-methylimidazo[1,2-a]pyridine.

IR (Nujol): 3400, 3325, 3280, 3125, 1635, 1558, 1515, 1500 cm$^{-1}$.

EXAMPLE 49

8-[2-Methyl-6-(2-hydroxyacetyl)aminobenzylamino]-3-(2-propynyl)-2-methylimidazo[1,2-a]pyridine.

IR (Nujol): 3375, 3220, 1690, 1590, 1560, 1520, 1500 cm$^{-1}$.

EXAMPLE 50

8-[2-Methyl-6-(2-hydroxypropionyl)aminobenzylamino]-3-(2-propynyl)-2-methylimidazo[1,2-a]pyridine.

IR (Nujol): 3390, 3330, 3300, 3100, 2110, 1680, 1580, 1560, 1520 cm$^{-1}$.

EXAMPLE 51

8-(2-Methyl-6-methoxycarbonylaminobenzylamino)-6-acetamido-3-(2-propynyl)-2-methylimidazo[1,2-a]pyridine, IR (Nujol): 3380, 3250, 3180, 1725, 1650, 1575 cm$^{-1}$.

EXAMPLE 52

To a mixture of 2,3-diamino-5-N,N-dimethylsulfamoyl)pyridine (0.61 g) and potassium carbonate (384 mg) in methanol (12.2 ml) was added 2-methyl-6-methoxycarbonylaminobenzyl chloride (0.6 g) and the resultant mixture was stirred at room temperature for 1.5 hours. After evaporating the solvent under reduced pressure, water was added to the residue and the mixture was extracted with chloroform. Chloroform was evaporated under reduced pressure from the extract. The residue was subjected to column chromatography on silica gel (40 g) and eluted with a mixture of chloroform and methanol (100:1). The fractions containing 2-amino-3-(2-methyl-6-methoxycarbonylaminobenzylamino)-5-(N,N-dimethylsulfamoyl)pyridine were combined and concentrated under reduced pressure. To the residue 3-mesyloxy-5hexyn-2-one (0.3 g) and methanol (0.8 ml) was added and the mixture was refluxed for 34 hours. After cooling, an aqueous solution of sodium bicarbonate was added thereto and the mixture was extracted with chloroform. The extract was subjected to column chromatography on silica gel (15 g) and eluted with a mixture of chloroform and methanol (100:1). The fractions containing the object compound were combined and concentrated under reduced pressure. The residue was triturated with diethyl ether to give 8-(2-methyl-6-methoxycarbonylaminobenzylamino)-6-(N,N-dimethylsulfamoyl)-3-(2-propynyl)-2-methylimidazo[1,2-a]pyridine (112 mg).

mp: 180° to 181° C. (decomp.).

IR (Nujol): 3400, 3300, 3250, 1690, 1550, 1515 cm$^{-1}$.

NMR (DMSO-d$_6$, δ): 2.30 (3H, s), 2.33 (3H, s), 2.62 (6H, s), 2.98 (1H, t, J=3 Hz), 3.57 (3H, s), 3.97 (2H, d, J=3 Hz), 4.42 (2H, d, J=5 Hz), 6.05 (1H, t, J=5 Hz), 6.27 (1H, s), 6.88–7.37 (3H, m), 7.97 (1H, s), 9.03 (1H, s).

EXAMPLE 53

To a solution of 8-(2-methyl-6-t-butoxycarbonylaminobenzylamino)-3-(2-propynyl)-2-methylimidazo[1,2-a]pyridine (8.42 g) in ethanol (67 ml) was added dropwise 23%-ethanolic hydrogen chloride (26 g) at room temperature and the mixture was stirred for 6 hours. The resultant solid was siolated by filtration and dispersed into a mixture of an aqueous solution of sodium bicarbonate and chloroform. The chloroform layer was separated and washed with water and dried over magnesium sulfate. Following filtration, the solvent was removed under reduced pressure to give 8-(2-methyl-6-aminobenzylamino)-3-(2-propynyl)-2methylimidazo[1,2-a]pyridine (4.08 g). The crude crystzals (0.5 g) were recrystallized from a mixture of chloroform and n-hexane to give 0.46 g of pure crystals.

mp: 199° to 201° C.

IR (Nujol): 3420, 3310, 3290, 3220, 1620, 1545 cm$^{-1}$.

NMR (DMSO-d$_6$, δ): 2.27 (6H, s), 2.91 (1H, t, J=3 Hz), 3.85 (2H, d, J=3 Hz), 4.30 (2H, d, J=5 Hz), 4.98 (2H, s), 5.61 (1H, t, J=5 Hz), 6.23–7.03 (5H, m), 7.60 (1H, d, J=7.5 Hz).

Analysis Calcd. for C$_{19}$H$_{20}$N$_4$: C 74.97, H 6.62, N 18.44. Found: C 74.56, H6.44 N 18.40.

EXAMPLE 54

To a solution of 8-(2-methyl-6-aminobenzylamino)-3-(2-propynyl)-2-methlimidazo[1,2-a]pyridine (0.26 g) in chloroform (7.8 ml) was added dropwise propionyl chloride (0.074 ml) at 1°–5° C. and the mixture was stirred for 5 hours at room temperature. The solvent was removed under reduced pressure and the residue was dispersed into a mixture of an aqueous solution of sodium bicarbonate and chloroform. The chloroform layer was separated and washed with water and dried over magnesium sulfate. Following filtration, the solvent was removed under reduced pressure and the residue was triturated with diethyl ether and collected by filitration to give 8-(2-methyl-6-propionylaminobenzylamino)-3-(2-propynyl)-2-methylimidazo[1,2-a]pyridine (0.25 g).

mp: 162° to 163° C.

IR (Nujol): 3375, 3300, 3225, 1645, 1555, 1530 cm$^{-1}$.

NMR (DMSO-d$_6$, δ): 1.03 (3H, t, J=7.5 Hz), 2.15–2.43 (2H, q, J=7.5 Hz), 2.28 (3H, s) 2.35 (3H, s), 2.92 (1H, t, J=3 Hz), 3.86 (2H, d, J=3 Hz), 4.33 (2H, d, J=5 Hz), 5.47 (1H, t, J=5 Hz), 6.29 (1H, d, J=7 Hz). 1H, t, J=7 Hz), 7.0–7.30 (3H, m), 7.58 (1H, t, J=7 Hz), 9.56 (1H, s).

Analysis Calcd for C$_{22}$H$_{24}$N$_4$O: C 73.31 N, 6.71, N 15.54. Found: C 73.32, N 6.86, N 15.33.

EXAMPLE 55

To a solution of 8-(2-methyl-6-aminobenzylaamino)-3-(2-propynl)-2-methylimidazo[1,2-a]pyridine (0.608 g) in chloroform (18 ml) was added dropwise benzoyl isothiocyanate (0.357 g) at 0° C. and the mixture was stirred for 3.5 hours. The solvent was removed under reduced pressure and the residue was triturated with diethyl ether to give a crystalline product. After chromatography on silica gel (20 g) with eluting with a mixture of chloroform and acetonitrile (50:1, V/V), the product was triturated with diethyl ether to give 8-[2-methyl-6-(3-benzoylthioureido)benzylamino]-3-(2-propynyl)-2-methylimidazo[1,2-a]pyridine (0.66 g).

mp: 165° to 166° C.

IR (Nujol): 3350, 3300, 3275, 1670, 1570, 1525 cm$^{-1}$.

NMR (CDCl$_3$, δ): 2.26 (3H, s,) 2.37 (3H, s), 2.90 (1H, t, J=3 Hz), 3.83 (2H, d, J=3 Hz), 4.33 (2H, d, J=5 Hz), 5.70 (1H, t, J=5 Hz), 6.33 (1H, d, J=7.5 Hz), 6.73 (1H, t, J=7 Hz), 7.13–7.76 (7H, m) 7.86–8.06 (2H, m) 10.5 (1H, broad s), 11.26 (1H, broad s).

The following compounds (Examples 56 to 76) were obtained according to a similar manner to that of Example 54 or Example 55.

EXAMPLE 56

8-[2-Methyl-6-(3-methylureido)benzylamino]-3-(2-propynyl)-2-methylimidazo[1,2-a]pyridine.

mp: 258° to 259° C.

IR (Nujol): 3375, 3325, 3295, 3210, 2100, 1695, 1560 cm$^{-1}$.

NMR (DMSO-d$_6$, δ): 2.28 (3H, s), 2.32 (3H, s), 2.61 (3H, d, J=4.5 Hz), 2.91 (1H, t, J=3 Hz), 3.86 (2H, d, J=3 Hz), 4.32 (2H, d, J=5 Hz), 5.31 (1H, d, J=5 Hz), 6.20–6.34 (2H, m), 6.69–7.30 (3H, m), 7.40–7.70 (2H, m), 7.93 (1H, s),

Analysis Calcd. for C$_{21}$H$_{23}$N$_5$O: C 69.78, H 6.41, N 19.38. Found: C 68.96, H 6.48, N 18.83.

EXAMPLE 57

8-(2-Methyl-6-formamidobenzylamino)-3-(2-propynyl)-2-methylimidazo[1,2-a]pyridine.

mp: 166° to 167° C.

IR (Nujol): 3400, 3210, 1690, 1605, 1580, 1555, 1535 cm$^{-1}$.

NMR (DMSO-d$_6$, δ): 2.28 (3H, s), 2.36 (3H, s), 2.91 (1H, t, J=3 Hz), 3.85 (2H, d, J=3 Hz), 4.37 (2H, d, J=5 Hz), 5.26–5.63 (1H, m), 6.31 (1H, d, J=7.5 Hz), 6.77 (1H, t, J=7.k Hz), 7.00–7.70 (4H, m), 8.35, 8.50 (1H, each s), 9.96, 10.10 (1H, each s).

Analysis Calcd. for C$_{20}$H$_{20}$N$_4$O: C 72.27, H 6.06, N 16.86. Found: C 71.89, H 6.23, N 16.36.

EXAMPLE 58

8-[2-Methyl-6-(2-acetoxypropionyl)aminobenzylamino]-3-(2-propynyl)-2-methylimidazo[1,2-a]pyridine.

mp: 140° to 141° C.

IR (Nujol): 3360, 3290, 1745, 1685, 1600, 1585, 1550, 1520 cm$^{-1}$.

NMR (CDCl$_3$, δ): 1.31 (3H,s), 1.44 (3H, d, J=7 Hz), 2.05 (1H, t, J=3 Hz), 2.38 (6H, s), 3.70 (2H, d, J=3 Hz), 4.33 (2H, d, J=5 Hz), 4.87 (1H, t, J=5 Hz), 5.21 (1H, q, J=7 Hz), 6.36 (1H, d, J=7 Hz), 6.76 (1H, t, J=7 Hz), 6.99 (1H, d, J=7 Hz), 7.23 (1H, t, J=7 Hz), 7.56 (1H, d, J=7 Hz), 7.80 (1H, d, J=7 Hz), 8.89 (1H, s)

EXAMPLE 59

8-[2-Methyl-6-(2--acetoxyacetyl)aminobenzylamino[-3-(2-propynyl)-2-methylimidiazo[1,2-a]pyridine.

mp: 155° to 158° C.

IR (Nujol): 3380, 3295, 1750, 1690, 1660, 1560, 1520 cm$^{-1}$.

NMR (CDCl$_3$, δ): 2.25 (3H, s), 2.03 (1H, t, J=3 Hz), 2.26 (3H, s), 2.39 (3H,s), 2H, d, J=3 Hz), 4.34 (2H, d, J=5 Hz), 4.56 (2H, s), 4.90 (1H, t, J=5 Hz), 6.36 (1H, d, J=7 Hz), 6.76 (1H, d, J=7 Hz), 7.0 (1H, d, J=8 Hz), 7.23 (1H, t, J=8 Hz), 7.56 (1H, d, J=7 Hz), 7.85 (1H, d, J=8 Hz), 9.0 (1H, s).

EXAMPLE 60

8-(2-Methyl-6-methoxycarbonylaminobenzylamino)-3-(2-propynyl)-2-methylimidazo[1,2-a]pyridine IR (Nujol): 3370, 3290, 1730, 1610, 1590, 1560, 1540 cm$^{-1}$.

EXAMPLE 61

8-(2-Methyl-6-acetamidobenzylamino)-3-(2-propynyl)-2-methylimidazo[1,2-a]pyridine.

IR (Nujol): 3370, 3290, 3220, 3125, 1637, 1555 cm$^{-1}$.

EXAMPLE 62

8-(2-Methyl-6-ureidobenzylamino)-3-(2-propynyl)-2-methylimidazo[1,2-a]pyridine.

IR (Nujol): 3260, 1650, 1560, 1100 cm$^{-1}$.

EXAMPLE 63

8(2-Methyl-6-t-butoxycarbonylaminobenzylamino)-3-(2-propynyl)-2-methylimidazo[1,2-a]pyridine.

IR (Nujol): 3350, 3310, 1705, 1550 cm$^{-1}$.

EXAMPLE 64

8-(2-Methyl-6-methoxycarbonylaminobenzylamino)-5-methyl-3-(2-propynyl)-2-methylimidazo[1,2-a]pyridine.

IR (Nujol): 3400, 3260, 1690, 1640, 1575, 1525 cm$^{-1}$.

EXAMPLE 65

8(2-Methyl-6-methoxycarbonylaminobenzylamino)-6-chloro-3-(2-propynyl)-2-methylimidazo[1,2-a]pyridine.

IR (Nujol): 3380, 3260, 1685, 1570, 1525 cm$^{-1}$.

EXAMPLE 66

8-(2-Methyl-6-methoxycarbonylaminobenzylamino)-5-acetamido-3-(2-propynyl)-2-methylimidazo[1,2-a]pyridine IR (Nujol): 3370, 3250, 1740, 1660, 1610, 1560, 1520 cm$^{-1}$.

EXAMPLE 67

8(2-Methyl-6-methoxycarbonylaminobenzylamino)-6-methoxycarbonyl-3-(2-propynyl)-2-methylimidazo[1,2-a]pyridine.

IR (Nujol): 3290, 1733, 1710, 1560, 1525, 1223 cm$^{-1}$.

EXAMPLE 68

8-(2Methyl-6-methoxycarbonylaminobenzylamino)-6-trifluoromethyl-3-(2-propynyl)-2-methylimidazo[1,2-a]pyridine.

IR (Nujol): 3360, 3230, 1730, 1600, 1565, 1530 cm$^{-1}$.

EXAMPLE 69

8(2-Methyl-6-methoxycarbonylaminobenzylamino)-6-nitro-3-(2-propynyl)-2-methylimidazo[1,2-a]pyridine.

IR (Nujol): 3400, 3300, 3260, 1690, 1640, 1565, 1525 cm$^{-1}$.

EXAMPLE 70

8-(2-Methyl-6-methoxycarbonylaminobenzylamino)-6-(N,N-dimethylsulfamoyl)-3-(2-propynyl)-2-methylimidazo[1,2-a]pyridine.

IR (Nujol): 3400, 3300, 3250, 1690, 1550, 1515 cm$^{-1}$.

EXAMPLE 71

8-[2-Methyl-6-(2-hydroxyacetyl)aminobenzylamino]3-(2-propynyl-2-methylimidazo[1,2-a]pyridine.

IR (Nujol): 3375, 3220, 1690, 1590, 1560, 1520, 1500 cm$^{-1}$.

EXAMPLE 72

8-[2-Methyl-6-(2-hydroxypropionylamino)benzylamino]3-(2-methylimidazo[1,2-a]pyridine.

IR (Nujol): 3390, 3330, 3300, 3100, 2110, 1680, 1580, 1560, 1520 cm$^{-1}$.

EXAMPLE 73

To a solution of 8-[2-methyl-6-(3-benzoylthioureido)-benzylamino]-3-(2propynyl)-2-methylimidazo[1,2-a]pyridine (0.59 g) in methanol (5.9 ml) and tetrahydrofuran (5.9 ml) was added a solution of potassium carbonate (0.174 g) in water (5 ml) and the mixture was stirred for 2 hours at room temperature. The solvent was removed under reduced pressure and the residue was dispersed into a mixture of water and chloroform. The chloroform layer was separated and washed with water and dried over magnesium sulfate. The residual oil was triturated with diethyl ether to give 8-(2-methyl-6-thioureidobenzylamino)-3-(2-propynyl)-2-methylimidazo[1,2-a]pyridine (0.36 g).

mp: 181° to 182° C.

IR (Nujol): 3400, 3325, 3280, 3125, 1635, 1558, 1515, 1500 cm$^{-1}$.

NMR (DMSO-d$_6$, δ): 2.28 (3H, s), 2.33 (3H, s), 2.92 (1H, t, J=3 Hz), 3.86 (2H, d, J=3 Hz), 4.29 (2H, d, J=5 Hz), 5,63 (1H, t, J=5 Hz), 6.31 (1H, d, J=7 Hz), 6.78 (1H, t, J=7 Hz), 6.90–7.60 (5H, m), 7.62 (1H, d, J=7 Hz), 9.48 (1H, s).

Analyusis Calcd. for C$_{20}$H$_{21}$N$_5$S: C 66.09, H 5.82 N 19.27. Found: C 66.45, H 6.04, N 18.84.

EXAMPLE 74

8-[2Methyl-6-(2-acetoxyacetyl)aminobenzylamino]3-(2-propynyl)-2 -methylimidazo[1,2-a]pyridine (0.33 g) was dissolved in a mixture of an aqueous solution (0.7 ml) of sodium carbonate (0.0118 g) and methanol (6.6 ml) at room temperature and then the mixture was stirred for 4 hours. The mixture was diluted with water and the resultant solid was collected to give 8-[2-methyl- 6-(2-hydroxyacetyl)aminobenzylamino]-3-(2-propynyl)-2-methylimidazo[1,2-a]pyridine (0.29 g).

mp: 195° to 196° C.

IR (Nujol): 3375, 3220, 1690, 1590, 1560, 1520, 1500 cm$^{=1}$.

NMR (DMSO-d$_6$, δ): 2.29 (3H, s), 2.32 (3H, s), 2.87 (1H, t, J=3 Hz), 3.82 (2H, d, J=3 Hz), 3.92 (2H, d, J=5 Hz), 4.26 (2H, d, J=6 Hz), 5.50 (1H, t, J=6 Hz), 5.68 (1H, t, J=5 Hz), 6.29 (1H, d, J=7 Hz), 6.71 (1H, t, J=7 Hz), 6.93–7.46 (3H, m), 7.54 (1H, d, J=7 Hz), 9.58 (1H, s).

Analysis Calcd. for C$_{21}$H$_{22}$N$_4$O$_2$: C 69.60, H 6.12, N 15.46. Found: C 69.73, H 6.25, N 15.37.

EXAMPLE 75

8-[2-Methyl-6-(2-hydroxypropionyl)aminobenzylamino]3-(2-propynyl)-2-methylimidazo[1,2-a]pyridine (0.37 g) was obtained from 8-[2-methyl-6-(2-acetoxypropionyl)aminobenzylamino]-3-(2-propynyl)-2-methylimidazoz[1,2-a]pyridine (0.43 g) according to a substantially similar manner to that of Example 73 or Example 74.

mp. 184° to 186° C.

IR (Nujol): 3390, 3330, 3300, 3100, 2110, 1680, 1580, 1560, 1520 cm$^{-1}$.

NMR (CDCl$_3$, δ): 1.3 (3H, d, J=6 Hz), 2.06 (1H, t, J=3 Hz), 2.25 (3H, s), 2.36 (3H, s,) 3.60 (2H, d, J=3 Hz), 4.20 (1H, q, J=6 Hz), 4.30 (1H, d, J=5 Hz), 5.20 (1H, d, J=5 Hz), 6.10 (1H, d, J=7.5 Hz), 6.60 (1H, t, J=7 Hz), 6.99 (1H, d, J=7.5 Hz), 7.16 (1H, d, J=7 Hz), 7.34 (1H, d, J=7 Hz), 7.67 (1H, d, J=7.5 Hz), 9.52 (1H, s).

Analysis Calcd. for C$_{22}$H$_{24}$N$_4$O$_2$: C 70.19, H 6.43, N 14.88. Found: C 69.76, H 6.3k, N 14.85.

EXAMPLE 76

To a mixture of iron powder (145 mg) and ammonium chloride (15 mg) in ethanol (12 ml) and water (2.2 ml) was added 8-(2-methyl-6-methoxycarbonylaminobenzylamino)-6-nitro-3-(2-propynyl)-2-methylimidazo[1,2-a]pyridine (360 mg) and the mixture was refluxed for 40 minutes. The inorgnic materials were removed by filtration and the solvent was evaporated under reduced pressure. An aqueous solution of sodium bicarbonate (5 ml) was added to the residue and the resultant solid was collected by filtration. The solid was dissolved in methylene chloride (10 ml) and acetic anhydride (94 mg) was added thereto. After stirring for 1 hour at room temperature, the organic layer was washed with an aqueous solution of sodium bicarbonate and then with water. The solvent was evaporated under reduced pressure. The residue was subjected to column chromatography on silica gel (10 g), eluting with a mixture of chloroform and methanol (100:3). The fractions containing the desired product were combined, and the solvent was removed under reduced pressure. The residue was triturated with a mixture of ethanol and diethyl ether (1:1) to give 8-(2-methyl-6-methoxycarbonylaminobenzylamino)-6-acetamido-3-(2-propynyl)-2-methylimidazo[1,2-a]pyridine (70 mg).

mp: 125° to 128° C.

IR (Nujol): 3380, 3250, 3180, 1725, 1650, 1575 cm$^{-1}$.

NMR (DMSO-d$_6$, δ): 2.07 (1H, t, J=3 Hz), 2.17 (3H, s), 2.32 (3H, s), 2.33 (3H, s), 3.65 (3H, s) 3.67 (2', d, J=3 Hz), 4.18 (2H, d, J=5 Hz), 4.88 (1H, t, J=5 Hz), 6.96 (1H, broad s), 6.90–7.73 (5H, me, 8.33 (1H, broad s).

EXAMPLE 77

To a solution of 8-(2-methyl-6-methoxycarbonylaminobenzylamino)-3-(2-propynyl)-2-methylimidazo[1,2-a]pyridine (0.5 g) in methanol (23 ml) was added dropwise 20%-ethanolic hydrogen chloride (0.5 ml) at 5°–10° C. and the mixture was stirred for 1 hour. A solid was collected to give 8-(2-methyl-6-methoxycarbonylaminobenzylamino)-3-(2-propynyl)-2-methylimidazo[1,2-a]pyridine hydrochloride (0.27 g).

mp: 235° to 237° C. (decomp.).

IR (Nujol): 3240, 3200, 3110, 3090, 3040, 2740, 2675, 2625, 2590, 2510, 1700, 1660, 1610, 1575, 1515 cm$^{=1}$.

NMR (DMSO-d$_6$, δ): 2.36 (3H, s), 2.45 (3H, s), 3.07 (1H, t, J=3 Hz), 3.56 (3H, s), 4.05 (2H, d, J=3 Hz), 4.36 (iH, broad s), 6.40 (1H, broad s), 6.86–7.46 (5H, m), 7.96 (1H, d, J=6 Hz), 9.03 (1H, s).

Analysis calcd. for C$_{21}$H$_{23}$ClN$_4$O$_5$: C 63.23, H 5.81, N 14.05, Cl 8.89. Found: C 63.30, H 6.05, N 13.97, Cl 8.80.

EXAMPLE 78

To a solution of 8-(2-methyl-6-methoxycarbonylaminobenzylamino)-3-(2-propynyl)-2-methylimidazo[1,2-a]pyridine (15 g) in acetone (115 ml) was added dropwise methanesulfonic acid (3.98 g) at 5°–10° C. and the mixture was stirred for 1 hour. A solid was collected to give methanesulfonic acid salt of 8-(2-methyl-6-methoxycarbonylaminobenzylamino)-3-(2-propynyl)-2-methylimidazo[1,2-a]pridine (12.88 g).

mp: 185° to 187° C. (decomp.).

IR (Nujol): 3310, 3225, 1740, 1710, 1710, 1660, 1600, 1575, 1530 cm$^{-1}$.

NMR (DMSO-d$_6$, δ): 2.25 (3H, s), 2.35 (3H, s), 2.45 (3H, s), 3.10 (1H, t, J=3 Hz), 3.57 (3H, s) 4.06 (2H, d, J=3 Hz), 4.35 (2H, d, J=3 Hz), 5.96 (1H, t, J=3 Hz), 6.87–7.46 (5H, m), 7.96 (1H, d, J=6 Hz), 8.98 (1H, s).

What we claim is:

1. An imidazopyridine compound of the following formula:

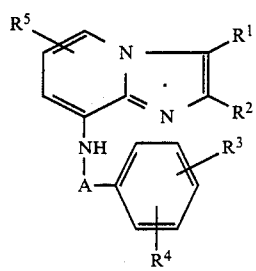

wherein
- R$^1$ is lower alkynyl,
- R$^2$ is lower alkyl,
- R$^3$ is lower alkyl,
- R$^4$ is amino or acylamino,
- R$^5$ is hydrogen; lower alkyl which may be substituted by halogen; nitro; amino; acylamino; esterified carboxy; or N,N-di (lower)alkylsulfamoyl, and
- A is lower alkylene, and a pharmaceutically acceptable salt thereof.

2. A compound of claim 1, wherein
   R$^5$ is hydrogen.

3. A compound of claim 2, wherein
   R$^4$ is amino, lower alkanoylamino, acyloxy (lower)alkanoylamino, hydroxy(lower)alkanoylamino, lower alkoxycarbonylamino, ureido, lower alkylureido, thioureido or aroylthioureido.

4. A compound of claim 3, wherein
   R$^4$ is amino, lower alkanoylamino, lower alkanoyloxy(lower)alkanoylamino, hydroxy(lower)alkanoylamino, lower alkoxycarbonylamino, ureido, 3-(lower)alklureido, thioureido or 3-aroylthioureido.

5. A compound of claim 4, wherein
   R$^4$ is lower alkoxycarbonylamino.

6. A compound of claim 5, wherein
   R$^1$ is 2-propynyl,
   R$^2$ is methyl,
   R$^3$ is methyl, and
   R$^4$ is methoxycarbonylamino, ethoxycarbonylamino or t-butoxycarbonylamino.

7. A compound of claim 6, which is 8-(2-methy-6-methoxycarbonylaminobenzylamino)-3-(2-propynyl)-2-methylimidazo[1,2-a]pyridine.

8. A compound of claim 4, wherein
   R$^4$ is lower alkanoyloxy(lower)alkanoylamino or hydroxy(lower)alkanoylamino.

9. A compound of claim 8, wherein
   R$^1$ is 2-propynyl,
   R$^2$ is methyl,
   R$^3$ is methyl, and
   R$^4$ is 2-acetoxyacetylamino, 2-acetoxypropionylamino, 2-hydroxyacetylamino or 2-hydroxypropionylamino.

10. A compound of claim 9, which is 8-[2-methyl-6-(2-hydroxypropionyl)aminobenzylamino]-3-(2-propynyl)-2-methylimidazo[1,2-a]pyridine.

11. A compound of claim 1, wherein
    R$^5$ is lower alkyl which may be substituted by halogen; halogen; nitro; amino; acylamino; esterified carboxy; or N,N-di (lower)alkylsulfamoyl.

12. A compound of claim 11, wherein
    R$^4$ is lower alkoxycarbonylamino,
    R$^5$ is lower alkyl, trihalo(lower)alkyl, halogen, nitro, amino, lower alkanoylamino, lower alkoxycarbonyl or N,N-di(lower)alkylsulfamoyl.

13. An antinlcerative pharmaceutical composition which comprises an effective amount of, a compound of claim 1 or a pharmaceutically acceptable salt thereof in admixture with a pharmaceutically acceptable carrier.

14. A method for the treatment of ulcers which comprises administering an effective amount of a compound of claim 1 or a pharmaceutically acceptable salt thereof to a human or animal.

* * * * *